US00PP10203P

United States Patent [19]

Shaw

[11] Patent Number: Plant 10,203

[45] Date of Patent: Jan. 20, 1998

[54] BRACHYCOME PLANT NAMED 'SUNBURST'

[75] Inventor: Patricia Valencia Shaw, Macgregor, Australia

[73] Assignee: Koala Blooms Pty. Ltd., Mordialloc, Australia

[21] Appl. No.: 705,602

[22] Filed: Aug. 30, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOVROM Disk 1997/02 Result Sheet ① 1997.

UPOVROM Disk 1997/02 Result Sheet ② 1997.

*Primary Examiner*—James R. Feyrer
*Assistant Examiner*—Kent L. Bell
*Attorney, Agent, or Firm*—C. A. Whealy

[57] ABSTRACT

A new and distinct Brachycome named 'Sunburst', characterized by its upright and spreading plant habit; fast crop time; moderate vigor; freely branching plant habit; numerous inflorescences with light yellow ray florets and bright yellow disc florets; long, erect peduncles that hold inflorescences above the foliage; and frost tolerance.

2 Drawing Sheets

The present invention relates to a new and distinct cultivar of Brachycome plant, botanically known as a Brachycome hybrid and named 'Starburst'. It is anticipated that the plant of this application will be marketed under the name "Billabong Sunburst".

The new cultivar is a product of a planned breeding program conducted by the inventor in MacGregor, South Brisbane, Australia. The objective of the breeding program was to develop new cultivars with yellow ray florets and frost tolerance.

The new cultivar originated from a cross made by the inventor of Brachycome sp. affinity curvicarpa, as the male or pollen parent, with *Brachycome segmentosa,* as the female or seed parent. The cultivar 'Sunburst' was discovered and selected by the inventor as a flowering plant within the progeny of the stated cross in a controlled environment in MacGregor, South Brisbane, Australia.

Asexual reproduction of the new cultivar by terminal cuttings taken in a polyethylene-covered greenhouse in MacGregor, South Brisbane, Australia, has shown that the unique features of this new Brachycome are stable and are reproduced true to type in successive propagations.

The new cultivar has not been observed under all possible environmental conditions. The phenotype may vary somewhat with variations in environment such as temperature, daylength and light intensity, without, however, any variance in genotype.

Compared to the parent cultivar Brachycome sp. affinity curvicarpa, plants of the new Brachycome are more compact; dense, not open plant form; and have paler yellow ray florets. Compared to the parent cultivar *Brachycome segmentosa,* plants of the new Brachycome are more compact, more floriferous, and have light yellow rather than white ray florets. A detailed comparison of the differences between *Brachycome segmentosa* and the cultivar 'Sunburst' appears in Chart A at the end of the specification.

The following characteristics have been repeatedly observed and are determined to be basic characteristics of 'Sunburst' which distinguish 'Sunburst' as a new and distinct cultivar:

1. Upright and spreading plant habit.
2. Fast crop time.
3. Moderate vigor.
4. Freely branching plant habit.

5. Numerous inflorescences with light yellow ray florets and bright yellow disc florets.
6. Long, erect peduncles that hold inflorescences above the foliage.
7. Frost tolerance.

The accompanying colored photographs illustrate the overall appearance of the new cultivar, showing the colors as true as it is reasonably possible to obtain in colored reproductions of this type.

The first photograph comprises a top perspective view of a single potted plant of 'Sunburst'.

The second photograph comprises a close-up view of inflorescences of plants of 'Sunburst'.

Floret color in the photographs may appear different from the actual floret color due to light reflectance.

The following observations, measurements, values, and comparisons describe plants grown in MacGregor, South Brisbane, Australia, under outdoor conditions with day temperatures ranging from 15 to 35° C. and night temperatures ranging from 10 to 30° C. and light levels from 5,000 to 9,000 footcandles. Color references are made to The Royal Horticultural Society Colour Chart except where general terms of ordinary dictionary significance are used.

Classification:

*Botanical.*—Brachycome hybrid cultivar 'Sunburst'.

*Commercial.*—Brachycome.

Parentage:

*Male or pollen parent.*—Brachycome sp. affinity curvicarpa.

*Female or seed parent.*—*Brachycome segmentosa.*

Propagation:

*Type.*—By cuttings.

*Time to initiate and develop roots.*—Summer: 10 to 20 days at temperatures of 25° C. Witer: 15 to 30 days at temperatures of 20° C.

*Rooting habit.*—Fibrous and freely branching.

Plant description:

*General appearance.*—Rounded, upright, spreading, herbaceous plant with broadly pinnatifid foliage and erect flower stems. Appropriate for 12.5 pots to 25-cm hanging basket containers. To produce a 15-cm finished flowering plant from rooted cuttings, 8 to 12 weeks are required depending on temperature and light level.

*Plant height.*—20 to 30 cm from soil level to top of inflorescences.

*Branching.*—Freely branching, typically 3 to 6 lateral branches develop when the terminal apex is removed (pinched). Lateral branches are typically 8 to 15 cm in length.

*Growth rate.*—Moderate.

*Vigor.*—Moderate.

*Foliage description.*—Arrangement: Alternate, single. Quantity. 15 to 30 per lateral branch. Leaf shape: Broadly pinnatifid, overall, oblong. Leaf apex: Acute to obtuse. Leaf base: Cuneate to obtuse. Leaf margin: Deeply lobed, faintly ciliate. Leaf aspect: Flat. Leaf length: About 5.2 cm. Leaf width: About 1.3 cm. Leaf texture: Smooth, glabrous. Leaf attachment: Sessile. Leaf color: Young leaves: Adaxial surface: 138A. Abaxial surface: 138B. Fully expanded leaves: Adaxial surface: 143A. Abaxial surface: 144A. Venation: Very faint, inconspicuous.

Flowering description:

*Inflorescence.*—Single daisy-type composite inflorescence form. Florets arranged acropetally on a capitulum. Inflorescences last on the plant for 3 to 4 weeks and for about 1 week as a fresh cut flower. Inflorescences self-cleaning.

*Natural flowering season.*—Natural flowering season is spring to early fall. Plants flower recurrently during this period.

*Quantity of inflorescences.*—One to five per lateral branch.

*Inflorescence diameter.*—2.6 to 3 cm.

*Inflorescence depth (height).*—0.8 to 1.1 cm.

*Fragrance.*—Not detectable.

*Ray florets.*—Quantity: 25 to 30 ray florets per inflorescence. Shape: Narrowly oblanceolate. Apex: Obtuse. Margin: Entire. Length: 8.4 to 9.8 mm. Width: About 2 mm. Texture: Smooth, glabrous. Color: When opening, abaxial surface: 5A to 5C. Mature, adaxial surface: 4D, with further development, florets maintain light yellow color, 4D. Mature, abaxial surface: 4D.

*Disc florets.*—Shape: Tubular. Diameter of disc: 8 to 9 mm. Disc floret length: About 4 mm. Disc floret width: About 1 mm. Color: Immature: 154A to 1A. Mature: 3A/5A. Number of disc florets per inflorescence: Numerous.

*Peduncle.*—Length: About 1 cm. Strength: Moderately strong, inflorescences held erect above foliage. Texture: Smooth, glabrous. Color: 144A.

*Flower bud.*—Shape: Globular. Length: About 5 mm. Diameter 5 to 6 mm. Color: 145C.

*Involucral bracts.*—Arrangement: Imbricated. Quantity: About 16 per inflorescence. Shape: Obovate. Apex: Obtuse. Margin: Scabrous, faintly ciliate. Texture: Smooth, glabrous. Color: Adaxial surface: 138C. Abaxial surface: 138B.

*Androecium.*—Stamen number: Five per floret. Anther shape: Linear. Anther length: About 1 mm. Anther color: 9B. Pollen color: 3A.

*Gynoecium.*—Pistil number: One per floret. Stigma shape: Bilobate. Style length: About 2.5 mm.

Disease Resistance: No susceptibility nor resistance to fungal, bacterial or viral pathogens has been noted.

Seed production: Seed production is typically not observed.

CHART A

| CHARACTERISTIC | 'SUNBURST' | *Brachycome segmentosa* |
|---|---|---|
| PLANT HEIGHT | 20 to 30 cm | 30 to 40 cm |
| VIGOR | Moderate | High |
| LATERAL BRANCH LENGTH | 8 to 15 cm | 10 to 30 cm |
| LEAF COLOR, YOUNG LEAVES, ABAXIAL SURFACE | 138A | 138A |
| LEAF COLOR, YOUNG LEAVES, ADAXIAL SURFACE | 138B | 138B |
| LEAF COLOR, MATURE LEAVES, ABAXIAL SURFACE | 143A | 144A |
| LEAF COLOR, MATURE LEAVES, ADAXIAL SURFACE | 144A | 144B |
| LEAF LENGTH | About 5.2 cm | About 4.5 cm |
| LEAF WIDTH | About 1.3 cm | About 1.7 cm |
| QUANTITY OF INFLORESCENCES PER LATERAL BRANCH | 1 to 5 | 1 to 2 |
| INFLORESCENCE DIAMETER | 2.6 to 3 cm | About 3.5 cm |
| RAY FLORET COLOR, OPENING | 5C | 155D |
| RAY FLORET COLOR, MATURE ABAXIAL SURFACE | 4D | 155D |
| RAY FLORET COLOR, MATURE ADAXIAL SURFACE | 4D | 69C |
| DISC FLORET COLOR, IMMATURE | 1A | 1A |
| DISC FLORET COLOR, MATURE | 3A to 5A | 2A |

It is claimed:

1. A new and distinct Brachycome named 'Sunburst', as illustrated and described.

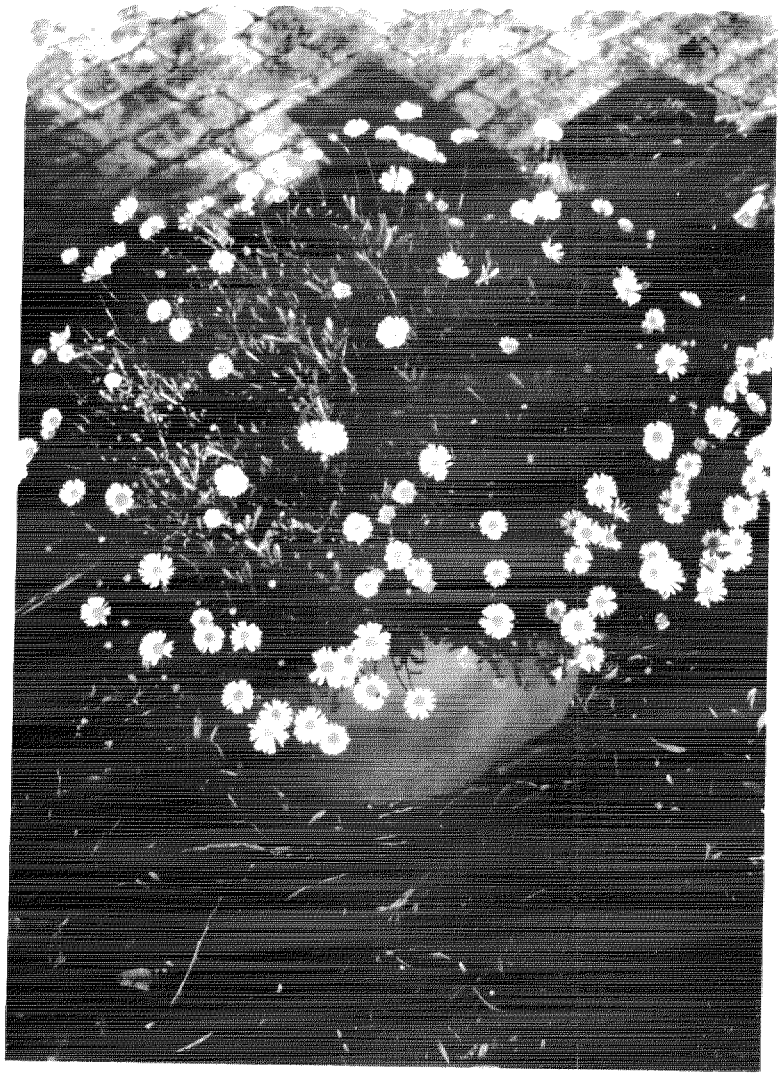

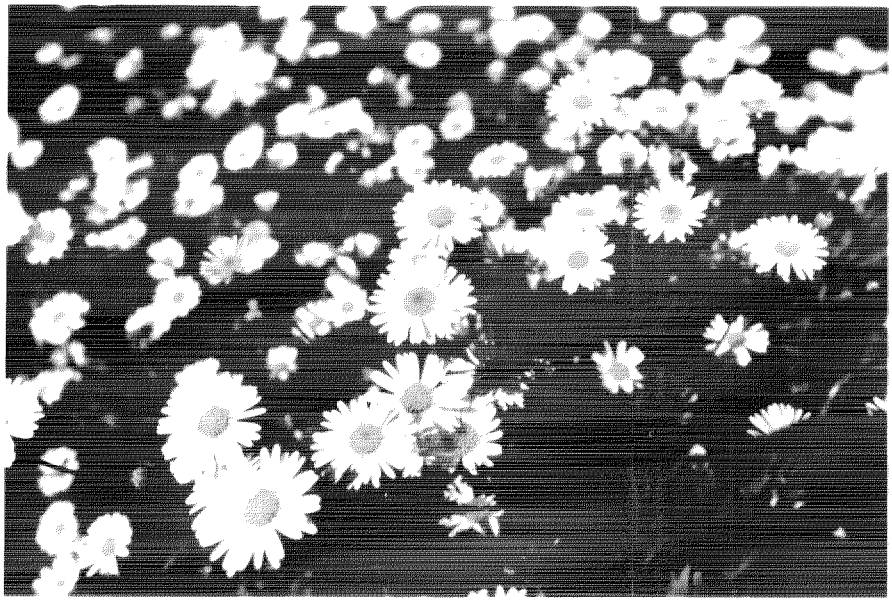

* * * * *